United States Patent [19]

Wong et al.

(10) Patent No.: US 7,103,144 B2
(45) Date of Patent: Sep. 5, 2006

(54) RADIOSURGERY X-RAY SYSTEM WITH COLLISION AVOIDANCE SUBSYSTEM

(75) Inventors: Phillip Wong, San Francisco, CA (US); James Wang, Fremont, CA (US); Sohail Sayeh, San Jose, CA (US)

(73) Assignee: Accuray, Inc., Sunnyvale, CA (US)

( * ) Notice: Subject to any disclaimer, the term of this patent is extended or adjusted under 35 U.S.C. 154(b) by 0 days.

(21) Appl. No.: 11/338,120

(22) Filed: Jan. 23, 2006

(65) Prior Publication Data

US 2006/0133572 A1     Jun. 22, 2006

(51) Int. Cl.
    *H05G 1/54* (2006.01)
(52) U.S. Cl. ...................................... 378/117
(58) Field of Classification Search .............. 378/62, 378/64, 68, 69, 95, 117, 193, 196, 197, 204, 378/206
    See application file for complete search history.

(56) References Cited

U.S. PATENT DOCUMENTS

| 5,207,223 A | 5/1993 | Adler ......................... 600/427 |
| 5,427,097 A | 6/1995 | Depp .......................... 600/427 |
| 5,485,502 A | 1/1996 | Hinton et al. ................ 378/117 |
| 5,878,112 A | 3/1999 | Koertge ....................... 378/209 |
| 6,272,368 B1 | 8/2001 | Alexandrescu ............... 600/407 |
| 6,651,279 B1 | 11/2003 | Muthuvelan ..................... 5/600 |
| 6,784,828 B1 | 8/2004 | Delcheccolo et al. ......... 342/70 |

FOREIGN PATENT DOCUMENTS

WO    WO 2005/099820 A1    10/2005

OTHER PUBLICATIONS

"PCT International Search Report", International Searching Authority, Jun. 21, 2005, PCT/US05/08658, 3 pgs.
"PCT Written Opinion of the International Searching Authority", International Searching Authority, Jun. 21, 2005, PCT/US05/08658, 5 pgs.

*Primary Examiner*—Courtney Thomas
(74) *Attorney, Agent, or Firm*—Blakely, Sokoloff, Taylor & Zafman LLP

(57) ABSTRACT

A method for preventing an emission head or arm assembly from entering an exclusion zone. The method may include calculating a variable dimension exclusion zone of a radiosurgery system, and preventing at least one of the emission head or arm assembly from entering the variable dimension exclusion zone. The method may also include establishing a exclusion zone of a radiosurgery system, the radiosurgery system comprising an x-ray source having an emission head, moving the emission head during treatment of a patient, wherein the exclusion zone travels with the emission head, and detecting a presence and location of an object in the traveling exclusion zone.

28 Claims, 8 Drawing Sheets

RADIOSURGERY X-RAY SYSTEM WITH COLLISION AVOIDANCE SUBSYSTEM

RELATED APPLICATIONS

This application claims the benefit of U.S. application Ser. No. 10/814,451, filed Mar. 31, 2004.

TECHNICAL FIELD

The present invention relates to radiosurgery and radiotherapy.

BACKGROUND

In radiosurgery, very intense and precisely focused doses of radiation in a beam from a source outside a patient's body are delivered to a target region in the body, in order to destroy tumorous cells. Typically, the target region consists of a volume of tumorous tissue. Radiosurgery requires an extremely accurate spatial localization of the targeted tumors. Radiosurgery offers obvious advantages over conventional surgery, during which a surgeon's scalpel removes the tumor, by avoiding the common risks and problems associated with open surgery. These problems include invasiveness, high costs, the need for in-hospital stays and general anesthesia, and complications associated with post-operative recovery. When a cancerous tumor is located close to critical organs, nerves, or arteries, the risks of open surgery are even greater.

As a first step in performing radiosurgery, it is necessary to deteIn1ine with great precision the location of tumors and any surrounding critical structures, relative to the reference frame of the treatment device. CT and MRI scans enable practitioners to precisely locate a tumor relative to skeletal landmarks or implanted fiducial markers. However, it is also necessary to control the position of the radiation source so that its beam can be precisely directed to the target tissue, with control of propagation in and through other body structures.

To effect such beam position control, stereotactic frames have been developed and used in the past for treatment of brain tumors. Stereotactic frames are rigid metal frames that are attached to the patient's skull and locked in place to provide a frame of reference for the surgeon during CT/MRI imaging, and for subsequent therapeutic treatment. A stereotactic frame is typically attached to the patient prior to scanning/imaging. The frame must remain in place while the surgeon is developing a computerized treatment plan, as well as during the actual treatment. During treatment, an x-ray or gamma ray source is precisely positioned with respect to the frame, so that the radiation can be administered according to the treatment plan.

While there are well-developed methods for attaching stereotactic frames to the skull for brain tumor treatment, attaching these frames to anatomical regions other than the skull in order to establish a stable frame of reference is too difficult to be practical. As one prior art example, a stereotactic frame that was deliberately constructed for the rest of the body (outside the head/neck region) required screws to be placed in the pelvis, incisions to be made along the spine to accommodate spinal clamps, and ten hours of general anesthesia to be administered to the patient while the frame was being attached to the patient, CT imaging performed, and radiosurgery undertaken. It is clearly not practical to perform such frame-based radiosurgery on areas other than the skull, and therefore the use of frame-based radiosurgery has so far been restricted to the treatment of intra-cranial tumors.

Despite the advantages of radiosurgery over open surgery, including significantly lower cost, less pain, fewer complications, no infection risk, no general anesthesia, and shorter hospital stays (most radiosurgical treatments are outpatient procedures), frame-based radiosurgery has a number of drawbacks. These drawbacks mostly relate to the use of the stereotactic frame. A stereotactic frame causes pain to the patient, since it has to be attached with screws. Also, a frame cannot be easily re-attached in precisely the same position for a subsequent radiation procedure, so that frame-based radio surgical treatment is limited to smaller tumors (generally less than about three centimeters in diameter) that can be treated in a single procedure. Moreover, the frame must remain in place from the time of diagnostic CT and/or MRI scanning, through the entire period of treatment, which may extend over a multi-day period. Finally, the biggest drawback is that frame-based radiosurgery cannot be used for tumors located outside of the head and neck region, because of the above-described difficulty of attaching these frames to anatomical regions other than the skull. Frame-based radiosurgery therefore cannot be used to treat ninety percent of all solid tumors, because they occur outside of the head/neck region.

These drawbacks have lead to the development of a frameless stereotactic radiosurgery system, exemplified by the CyberKnife system (henceforth "CyberKnife") made by Accuray, Inc., Sunnyvale, Calif. CyberKnife is an image guided robotic system which eliminates the need for the rigid stereotactic frames described above, and enables the treatment of extra-cranial tumor sites. CyberKnife provides numerous advantages compared to conventional stereotactic radiosurgery systems, including but not limited to: ability to treat tumors throughout the body, not just those located within the head/neck region; increased access to, and coverage of, any target volume; ability to treat tumors that are larger than about three centimeters in diameter; minimal constraints on patient set-up; ability to deliver a plurality of fractionated treatments; and enhanced ability to avoid damaging critical structures.

CyberKnife includes a robotic system onto which an x-ray linear accelerator ("linac") is mounted, and a controller. The linac is adapted to selectively provide a precisely shaped and timed radiation beam. The controller uses CT and possibly MRI data, or other types of image data, that define the target tissue and important other bodily structures, together with treatment planning and delivery software to identify a series of landmarks within the treatment region, prior to surgery. CyberKnife may further include a stereo x-ray imaging system, which during treatment repeatedly measures the 10cation and orientation of these landmarks relative to the linac. Prior to the delivery of radiation at each delivery site, the controller directs the robotic system to adjust the position and orientation of the linac in accordance with the measurements made by the x-ray imaging system, so that a desired series of radiation beams can be applied to the body, optimally dosing the target tissue while minimizing radiation to other body structures. In this way, CyberKnife allows accurate delivery of high doses of radiation, without requiring a stereotactic frame.

It is important to ensure that during the successive positionings of the linac during a treatment, the robotic system does not collide with objects (for example, parts of the patient's body, its own structure, or other equipment in the treatment room). Since patient setup is minimally constrained by a frameless radiosurgery system, it is difficult to have complete knowledge of the patient's body position when preparing a treatment plan, particularly regarding their arms and legs. An obstacle detection/collision avoidance system would therefore be desirable in frameless radiosurgery systems such as the CyberKnife, Because of its ability to deliver fractionated treatments, CyberK11ife is well adapted for radiotherapy, as well as for radiosurgery. The term radiotherapy refers to a procedure in which radiation is applied to a target region for therapeutic, rather than necrotic, purposes. The amount of radiation utilized in radiotherapy is typically about an order of magnitude smaller, as compared to the amount used in radiosurgery. Radiotherapy is frequently used to treat early stage, curable cancers. In addition to delivering radiation to cancerous tissue, radiotherapy systems generally also irradiate a certain amount of normal tissue surrounding the tumor. Typically, a series of relatively small doses are delivered over a number of days. Each radiation dose not only kills a little of the tumor, but also creates some collateral damage to healthy surrounding tissue, which however usually heals by itself, because it has a greater ability to repair, compared to cancerous tissue.

A collision avoidance system, referred to above, would also be desirable when CyberKnife is being used for radiotherapy, as well as for radiosurgery. For convenience, the term "radiosurgery" in this application shall henceforth mean "radiosurgery and/or radiotherapy."

The present invention provides a frameless radiosurgery system having a collision avoidance subsystem.

In an exemplary embodiment, a frameless radiosurgery system in accordance with the present invention includes an x-ray source, and a robot. The robot includes an arm assembly extending from a base unit. The x-ray source, which in a preferred form is a linac, has an emission head mounted at a distal end of the arm assembly. The x-ray emission head is adapted for selectively emitting an x-ray beam along a beam axis. The arm assembly may be articulated (i.e., have a series of rigid elements linked by rotatable couplings), may be flexible (i.e., have a series of rigid or flexible elements linked by flexible couplings), or may be a combination of both articulated and flexible portions.

The radiosurgery system further includes an associated controller for selectively orienting the x-ray emission head whereby the x-ray beam extends along a succession of treatment axes. The radiosurgery system further includes a collision avoidance subsystem, including means for preventing the x-ray emission head and the arm assembly from effecting a collision with an object in one or more predefined exclusion zones.

In one exemplary embodiment of the invention, the collision avoidance subsystem includes a light source (such as a laser or an LED (light-emitting-diode) effective to establish a substantially planar (or sheet-like) light beam between the exclusion zone and the emission head. The planar light beam may be fan-shaped. In this embodiment, the controller is responsive to observation of an object extending through the light beam, to interrupt any further motion of the head toward the exclusion zone. The light source may be fixedly positioned with respect to the x-ray emission head, defining an exclusive zone that "travels" with the head. Alternatively, the light source may be fixedly positioned with respect to the base unit of the robot, for example by being mounted on a wall of the treatment room, defining an exclusive zone that is fixed with respect to the treatment room.

In another embodiment of the invention, the collision avoidance subsystem includes a least one optical emitter-receiver pair that is effective to detect the breaking of a light beam when an object extends into the one or more exclusion zones. The optical emitter is a light source, as described in paragraph 15 above. The optical receiver is constructed and arranged to receive light that 1) has reached an object that has intruded into one or more of the exclusion zones, and 2) is back-scattered from the object.

In another embodiment of the invention, the collision avoidance subsystem includes a laser range finder that can detect movement of an object into a light beam. The laser rangefinder includes a transmitter that generate laser light and transmits the light toward one or more exclusion zones, and a receiver/photodetector for receiving and detecting laser light that is backscattered from any object that intrudes into the one or more exclusion zones. The laser range finder includes means for determining, from the received backscattered laser light, the distance to the object.

In another embodiment of the invention, a plurality of exclusion zones may be defined. In other words, multiple "layers" of exclusion zones may be defined. In one of many possible exemplary embodiments, a first "shell-like" exclusion zone may be defined which slows down the motion of the head. In this exemplary embodiment, a second exclusion zone may be defined, which completely stops any further motion of the head, when the head reaches one or more boundaries between the first exclusion zone and the second exclusion zone. In another embodiment of the invention, at least one of the exclusion zones is not a static zone, but rather is a variable dimension exclusion zone. In another embodiment of the invention, the collision avoidance subsystem includes an array of acoustic transducers fixedly coupled to the x-ray emission head. Each of the transducers transmits a succession of acoustic pulses along a transmission axis extending from the head, and detects acoustic energy backscattered along the transmission axis from an object disposed along the transmission axis. The beam axes are mutually aligned whereby cross-sections of adjacent pairs of the pulses transverse to the transmission axis are contiguous at a predetermined distance from the head. In this embodiment, the collision avoidance subsystem includes means for determining, from the received backscattered acoustic energy, the distance between the head and the object.

The collision avoidance subsystem further includes means for inteJ111pting, in response to the determined distance being at or less than a predetermined value, any further motion of the head toward the exclusion zone.

In another embodiment of the invention, the collision avoidance subsystem includes a sensor disposed on a surface of the articulated arm assembly. The sensor is operative to generate an alarm signal upon impact of the sensor with an object, during motion of the arm assembly and/or the x-ray emission head. The subsystem further includes means responsive to the alaln1 signal to interrupt any further motion of the arm and/or head. The sensor may be a tactile sensor, or other type of sensor adapted for proximity sensing. By way of example, the sensor may consist of a fluid-filled bladder, and a pressure transducer coupled to the bladder, in one embodiment of the invention. In other embodiments, the sensor may be an infrared (IR) sensor, or an electrostatic capacitance sensor.

In any of the above described collision avoidance systems, the detection of breach of the exclusion zone and the system's response to such detection may be automatic (e.g., under control of the controller) or may be manually implemented (e.g., when a human observer detects a breach, that observer initiates the system response (e.g., halting further advance of the head).

BRIEF DESCRIPTION OF THE DRAWINGS

The present invention is illustrated by way of example, and not by way of limitation, in the figures of the accompanying drawings.

DETAILED DESCRIPTION

The present invention provides a frameless radiosurgery system including an x-ray source and an associated robot positioning system and a collision avoidance subsystem. The collision avoidance subsystem prevents the x-ray source, the robot system, or components of the robot system, from colliding with any critical components (for example the patient, or parts of the radiosurgery system, or other equipment).

Figure 1:
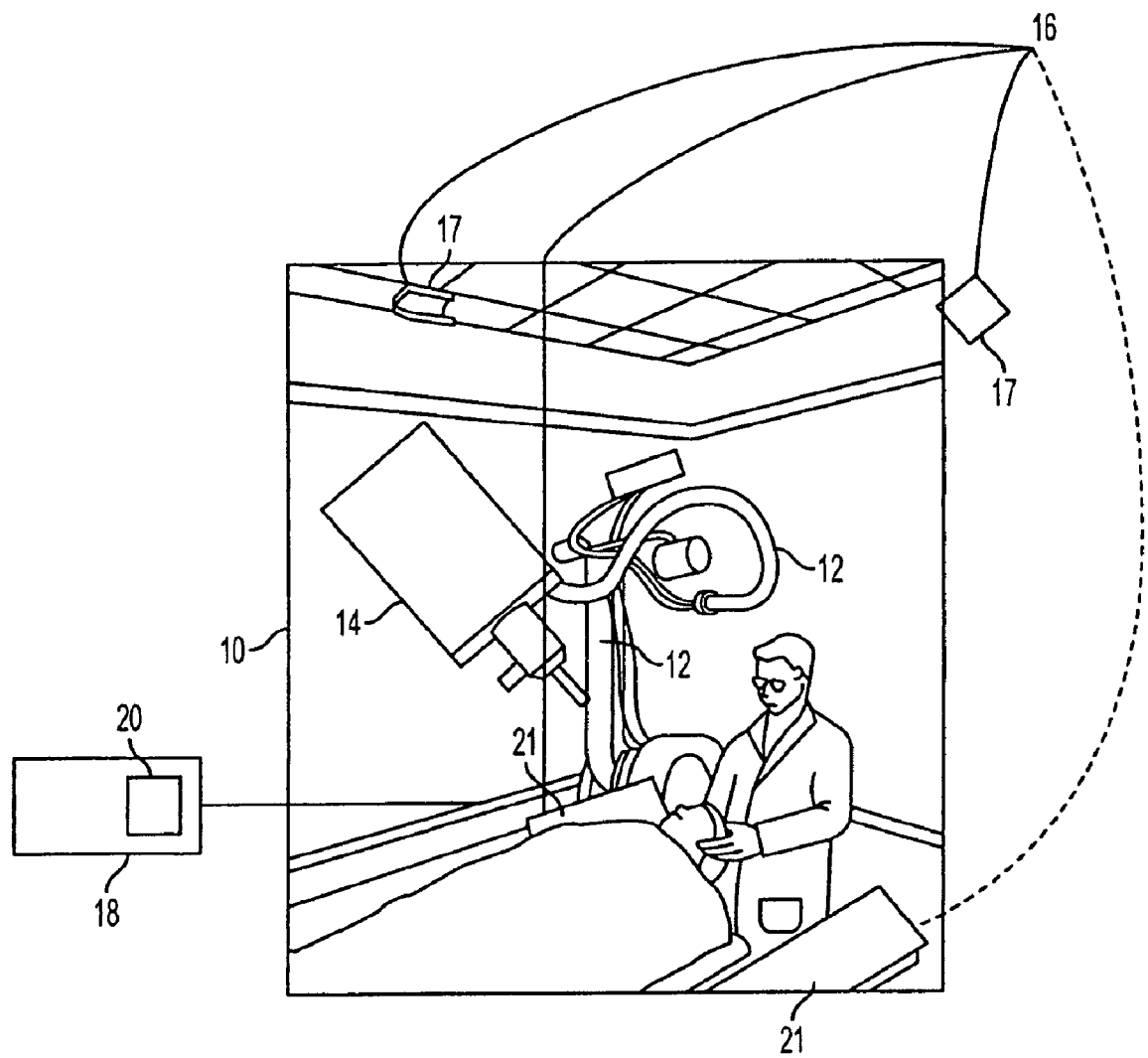
FIG. 1 illustrates a frameless stereotactic radiosurgery system known in the prior art.

FIG. 1 illustrates a frameless stereotactic radiosurgery (and/or radiotherapy) system 10 known in the art. An exemplary radiosurgery (and/or radiotherapy) x-ray system is described in commonly-owned U.S. Pat. No. 5,207,223 and in commonly-owned U.S. Pat. No. 5,427,097.

In overview, the radiosurgery system 10 includes: a robot system 12, having a fixed base and including an articulated arm assembly; a radiation source 14 mounted at the distal end of the articulated arm assembly; a stereo x-ray imaging system 16; and a controller 18. The radiation source 14 is preferably an x-ray linear accelerator ("linac"). The stereo x-ray imaging system 16 typically consists of a pair of x-ray sources 17, and a pair of x-ray image detectors 21, each detector being opposite an associated one of x-ray sources 17. The controller 18 contains treatment planning and delivery software 20, which is responsive to CT and/or MRI data and user input to generate a treatment plan consisting of a succession of desired beam paths, each having an associated dose rate and a duration at each of a fixed set of nodes. In response to the controller's directions, the robot 12 moves (and orients) the x-ray source and controls beam intensity, successively and sequentially through each of the nodes, while delivering the associated dose.

Figure 2:
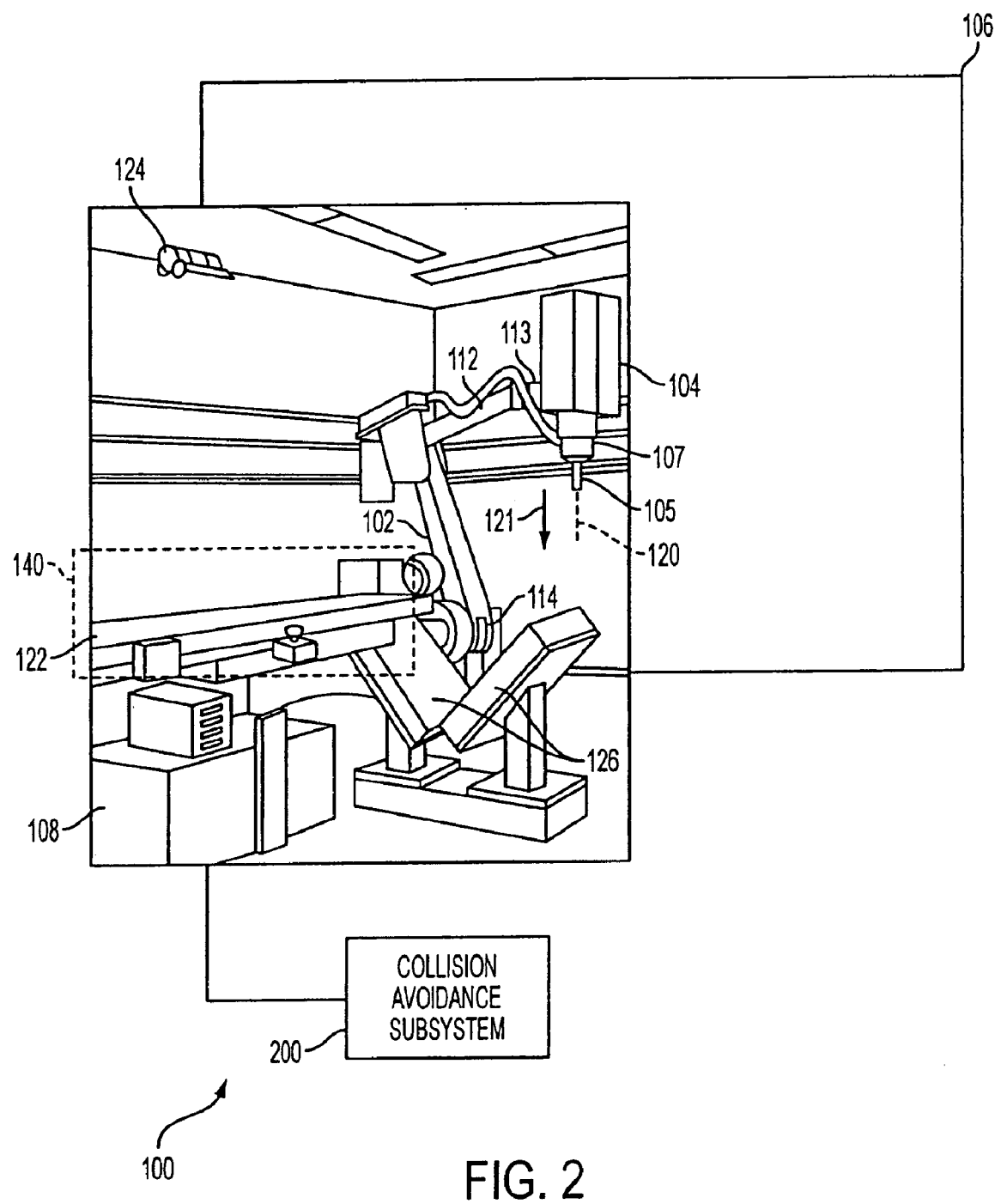
FIG. 2 illustrates a frameless stereotactic radiosurgery x-ray system including a collision avoidance subsystem, constructed in accordance with an exemplary embodiment of the present invention.

FIG. 2 illustrates a frameless stereotactic radiosurgery x-ray system 100 that is similar to system 10 but further includes a collision avoidance subsystem 200, constructed in accordance with an exemplary embodiment of the present invention. In overview, the radiosurgery x-ray system 100 in the illustrated embodiment includes a robot system 102; a radiation source 104; an x-ray imaging system 106; a controller 108; and a collision avoidance subsystem 200. A patient positioning table 122 may support the patient relative to the x-ray imaging system 106 and other equipment. Once in position, the position table 122 remains fixed throughout the treatment.

Typically, the robot system is an industrial robot/manipulator 102. For example, a Fanuc 420 or Kuka 210 may be used. In the preferred form, the robot system 102 includes an articulated arm assembly 112 extending to a distal end 113 from a base unit 114, affixed to the floor of the treatment room. The radiation source 104 is mounted at the distal end 113 of the arm 112.

Preferably, the radiation source is a small x-ray linac (linear accelerator) 104. Typically, the linac 104 includes a waveguide, through which microwave radiation is fed in, so as to accelerate electrons. The electrons may be produced by a pulsed electron gun, by way of example. The linac 104 includes an x-ray emission head 105 adapted for selectively emitting an x-ray beam 120 along a beam axis 121. The linac 104 also includes a collimator 107 for collimating the x-ray beam 120, before the beam 120 is delivered to the desired treatment region. The linac 104 typically weighs about 100 kg, although other weight ranges are also within the scope of the present invention.

The x-ray imaging system 106 may include two x-ray sources 124 mounted to the ceiling of the treatment room, and a pair of x-ray image detectors 126 mounted orthogonally, typically on the floor. Each of the detectors 126 is opposite an associated one of x-ray sources 124. The x-ray image detectors 126 may be amorphous silicon image detectors or cameras.

The controller 108 includes the software operating system for the frameless radiosurgery system 100. The controller 108 may be a dual processor computer, which performs numerous functions, including but not limited to: 1) performing treatment planning: 2) providing 3-D displays of images (e.g., from x-ray data); 3) calculating the requisite dose at each desired node; 4) controlling the x-ray linac and the robotic arm; 5) managing and recording the treatment; and 6) monitoring the equipment for patient safety.

Before the radiosurgery treatment, a CT scan is taken of the tumor region, i.e. of the portion of the patient's anatomy that contains the tumors of interest. A set of digitally reconstructed radiographs (DRRs) are generated for the tumor region, based on the pre-operative CT scan. DRRs are artificial, synthesized 2D images that represent the shadow graphic image of the tumor that would be obtained, if imaging beams were used having the same intensity, position, and angle as the beams used to generate real time radiographic images of the tumor, and if the tumor were positioned in accordance with the 3D CT scan.

The image detectors 126 then obtain live ("real-time") radiographic images, by capturing x-ray images from the ceiling-mounted x-ray sources 124. The controller 108 correlates these live radiographic images with the pre-computed array of synthetic radiographs, and directs the robot 102 to adjust the position of the linac 104 accordingly.

In other words, patient location and movement is tracked by the matching the "live" x-ray images to the pre-computed set of synthetic images that correspond to various projected movements of the patient. Standard image processing techniques are used to subtract the images and obtain a measure of the differences between the images.

The resulting imaging information is transferred to the robot 102 by the controller 108, which directs the robot 102 to compensate for any changes in patient position by repositioning the linac 104. Under the directions of the controller 108, the articulated arm assembly 112 manipulates the linac 104 in order to accommodate tumor movement, caused by patient movement. In this way, the controller 108 selectively orients the emission head 105 of the linac 104, whereby the emitted x-ray beam extends along a succession of treatment axes, in order to destroy tumors located within the pre-scanned treatment region. The treatment axes are disposed in a patient zone surrounding the patient.

While the articulated arm assembly 112 of the robot 102 moves around in order to adjust the position of the linac 104, in response to directions from the controller 108, it is important to prevent any part of the robotic system 102, and the linac 104, from colliding with other objects in the treatment room. These objects may include, but are not limited to, other parts of the patient's body, and other equipment such as the patient positioning system. As just one example, in a radiosurgery session for treating tumors in the stomach, it is desirable to prevent the x-ray linac 104 or the arm assembly 112 from colliding with the head of the patient, while the arm assembly 112 is maneuvering the x-ray beam into a correct position.

Accordingly, in one form, the present invention features a collision avoidance subsystem 200 for detecting, and responding to, the relative passage of the x-ray source or any part of the robot system 102 into a predefined exclusion zone 140. In this form of the invention, the exclusion zone 140 is fixed relative to, and surrounds (at least in part) the patient. In another form of the invention, a predefined exclusion zone 140 is fixed with respect to, and travels with, the emission head (the x-ray source). In this form, collision detection subsystem 200 detects, and responds to, relative passage of any object (e.g., the patient or equipment or any other object) into the exclusion zone. In both forms, the collision avoidance system 200 prevents collision of any part of robot system and/or x-ray source with any object in the exclusion zone 140. In one embodiment, the collision avoidance system 200 detects intrusion of an object into the exclusion zone 140 and upon such detection, prevents or slows down further relative advance of such object in the exclusion zone.

In one embodiment, the collision avoidance system 200 is effective to prevent the radiosurgical (or radiotherapeutic) x-ray head itself from entering the exclusion zone(s), instead of preventing the collision between an object and any part of the robot system and/or x-ray source within the exclusion zone.

In the present invention, in order to establish an exclusion zone, a computer-aided design (CAD) model of the room used for radiosurgery treatment is set up by the operating system in the controller 108, prior to treatment. During set-up of the CAD model of the treatment room, the exclusion zone 140 is computed by the treatment planning software in the controller 108. The exclusion zone 140 defines a region surrounding the patient within which neither the x-ray linac 104 nor the articulated arm assembly 112 of the robot system 102 may enter. A number of parameters may be used in the computation of the exclusion zone 140, including but not limited to: the size and dimensions of the patient; the expected movements of the patient during treatment; and the location of the patient positioning system 122. This exclusion zone can be updated in real time by feedback from, for instance, the patient positioning system 122.

In an exemplary embodiment of the invention (not illustrated), more than one exclusion zone may be computed and defined. In other words, a plurality (or multiple "layers") of exclusion zones may defined. In just one of many possible examples and variations, a first "shell-like" exclusion zone may be defined in which the motion of the head is slowed down, but not completely halted. A second exclusion zone may be defined, which completely stops any further motion of the head, when the head reaches the boundary between the first exclusion zone and the second exclusion zone.

Figure 3A:
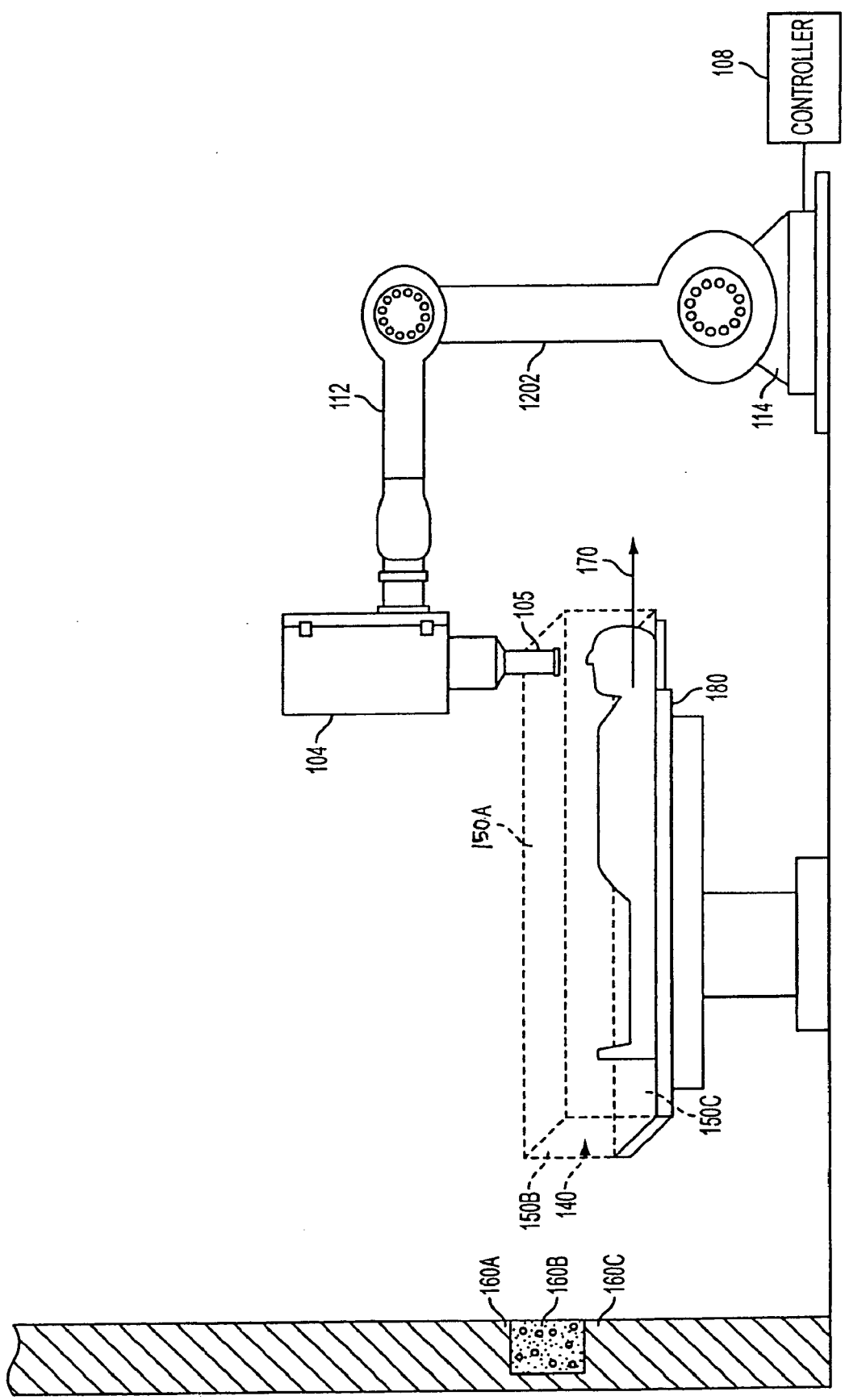
FIG. 3A illustrates a collision avoidance subsystem, in which a light source is fixedly positioned with respect to the base unit of a robot that manipulates the position of the x-ray linac.

In an embodiment of the invention illustrated in FIG. 3A, the collision avoidance subsystem 200 uses one or more light sources to define the exclusion zone 140. In this embodiment, the one or more light sources are effective to establish a set of substantially planar (or sheet) light beams between the pre-computed exclusion zone 140 and the x-ray emission head 105 of the linac 104, by sweeping one or more linear light beams into substantially planar pattern light beams. In the illustrated embodiment, one or more light sources are fixedly positioned with respect to the base unit 114 of the robotic system 102. For example, the light sources may be mounted to a wall of the treatment room. The light sources establish a substantially planar light beam by sweeping a linear light beam along a plane.

By way of example, a "rectangular" exclusion zone 140 is illustrated in FIG. 3A.

As shown in FIG. 3A, the exclusion zone 140 is defined by three distinct planar light beams, 150A, 150B, and IS0C. Each planar light beam extends from a respective one of line sources 160A, 160B, and 160C, mounted to the wall, where each "line source" is a plurality of light sources (lasers or LEDs) that are lined up to form a "line" of light sources. The principal plane of beam 150A is perpendicular to the principal plane of beam 150B, which is perpendicular to the principal plane of beam 150C, establishing an inverted V-shaped channel extending about the exclusion zone 140 and parallel to a patient axis 170 of the exclusion zone 140. The dimensions of the beams 150A, 150B, and 150C are such that a patient lying along axis 170 on a table beneath the zone 140 is wholly within the zone 140.

In the illustrated embodiment, the beams 1S0A, 150B, and 150C may be formed by a linear array of light sources (such as lasers or LEDs) extending along each of 160A, 160B, and 160C. Alternatively, each of the planar beams 150A, 1S0B, and 150C may be formed from a single light source (such as a laser or an LED) for each beam, which is repetitively swept in the principal planes of these beams.

In one embodiment (not illustrated), the collision avoidance system includes at least one optical emitter-receiver pair that is capable of detecting the breaking of a light beam as the light beam reaches an object within an exclusion zone, and is scattered off that object. In this form of the invention, at least one of the light sources (described in paragraphs 44–46 above) is provided with a corresponding light receiver (not illustrated). The light receiver receives light from a light beam that was generated by the light source (i.e. the "emitter" in the emitter-receiver pair), then was "broken" by reason of being incident upon an object extending through one of the exclusion zones, and of being back-scattered by that object. A photodetector may be coupled to the light receiver, to detected the intensity of the back-scattered light.

In another embodiment of the invention (not illustrated), the collision avoidance subsystem includes a laser rangefinder (or equivalently a lidar, an acronym that stands for LIght Detection And Ranging) that can detect movement of an object into a light beam defining the exclusion zone. As known in the art, a laser rangefinder is a laser device that can accurately measure the distance to an object by sending out light to the object and analyzing the light that is reflected/scattered off of the object. The range to the object is determined by measuring the time for the light to reach the object and return.

In this embodiment, the laser rangefinder may include: 1) a transmitter that generates laser light and transmits the laser light toward one or more exclusion zones, or toward one or more boundaries of the exclusion zone; 2) a receiver for receiving the transmitted light that is back-scattered from any object that intrudes into the one or more exclusion zones; 3) a photodetector for detecting the intensity of the light received by the receiver; and 4) a data acquisition system, effective to compute the distance to the object by making time-or-flight measurements, i.e. by measuring the time required for the light to reach the object and return.

The transmitter includes a laser source for generating laser light. For example, a diode-pumped Nd—YAG (neodymium-yttrium-aluminum-garnet) laser may be used; however, any other commercially available laser source may be used. The transmitter may also include a light-beam steering unit for directed the generated laser light towards the desired exclusion zone or boundary thereof. The receiver may be any conventional light receiver that is commercially available. The photodetector may be a photomultiplier tube or avalanche photodiode. The data acquisition system may include a time-of-flight electronics unit (including one or more amplifiers, a clock oscillator, one or more filters, a digitizer, and a demodulator) and a microprocessor controller.

In one form, the transmitter component of the laser range finder may be coupled to the x-ray emission head. In this form of the invention, the transmitter generates and transmits a laser pulse along a light axis extending from the head, and detects laser light back-scattered along the light axis from an object disposed along the light axis. The receiver, detector, and data acquisition components of the laser rangefinder determines, from the received backscattered laser light, the distance between the head and the object. The microprocessor controller unit may include means for interrupting, in response to the determined distance being at or less than a predetermined value, any further motion of the head toward the exclusion zone.

In one form, a doppler lidar may be used to measure the velocity of the object, as the object moves into or within the one or more exclusion zones. When the light transmitted from the lidar hits a target moving towards or away from the lidar, the wavelength of the light reflected/scattered off the target is slightly changed. (If the object is moving away, the return light has a longer wavelength; if the object is moving closer towards the lidar, the return light has a shorter wavelength.) The doppler lidar is effective to measure the resulting Doppler shift, and hence determine the velocity of the object.

In a manually controlled subsystem 200, the controller 108 is responsive to a user action, taken in response to observation of an object extending within the exclusion zone 140, to interrupt any further motion of the x-ray emission head 105 toward the exclusion zone 140. In other words, the user may press a switch or a button, as soon as the user observes any object extending within the exclusion zone. In response, the controller 108 directs the robotic system to interrupt any further movement of the arm assembly 112 (and hence of the emission head 105 mounted at the distal end 113 thereof) toward the exclusion zone 140.

Alternatively, the collision avoidance subsystem 200 may be an automatically activated system, in which the interception of any object extending within the exclusion zone 140 automatically triggers a shut-off response by the controller 108. The shut-off response prevents any further motion of the arm assembly 112 toward the exclusion zone 140.

Figure 3B:
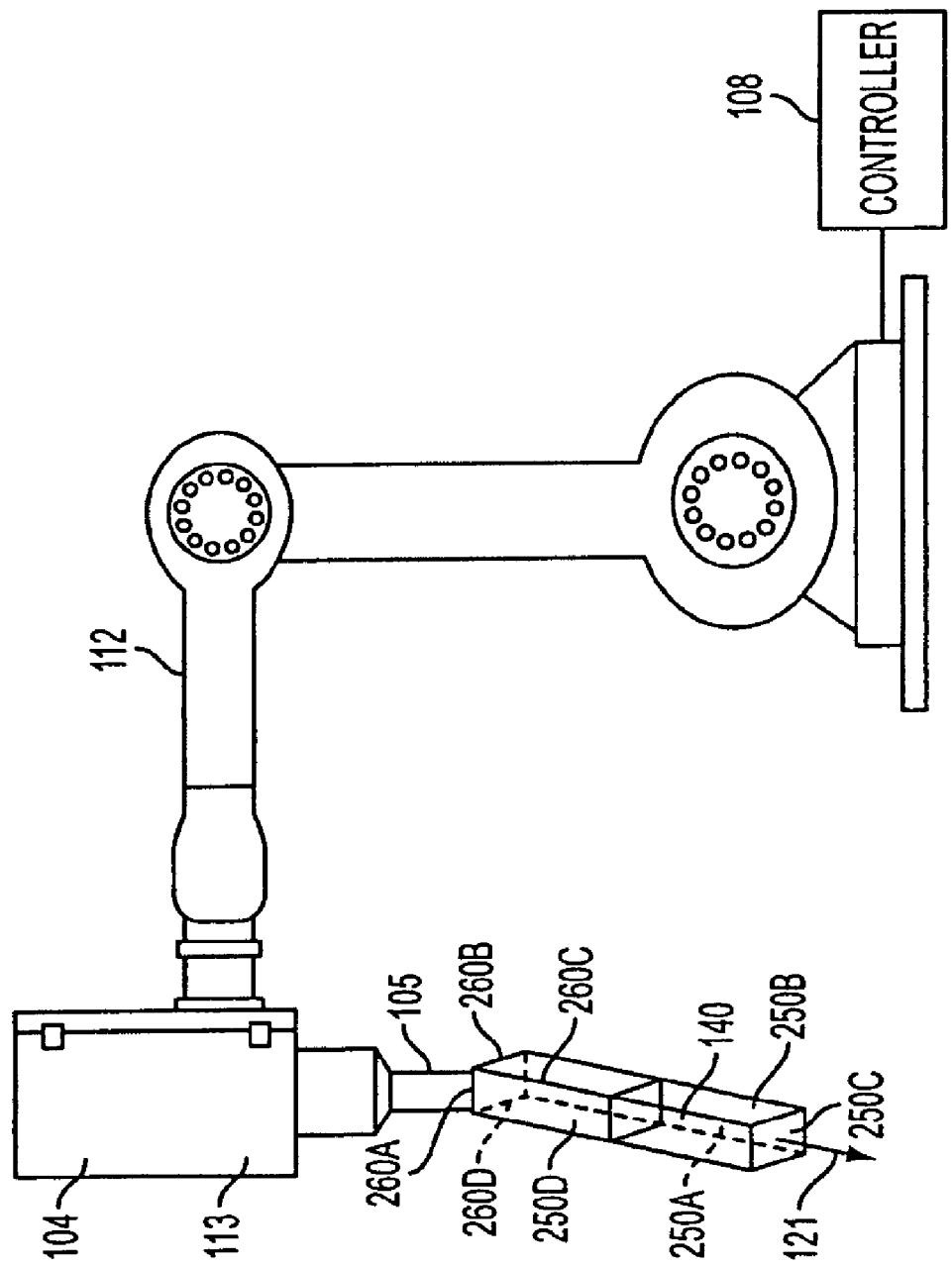
FIG. 3B illustrates a collision avoidance subsystem, in which a light source is fixedly positioned with respect to the x-ray emission head of an x-ray linac.

In another embodiment, illustrated in FIG. 3B, a light source may be fixedly positioned with respect to the emission head 105 of the x-ray linac 104. For example, a light source may be mounted at the distal end 113 of the arm assembly 112, next to the x-ray linac 104. In this embodiment, the light source defines an exclusive zone that "travels" with the bead.

By way of example, a rectangular exclusion zone 140 may be defined which is attached to, and travels with, the head 113, as illustrated in FIG. 3B. In the illustrated exemplary embodiment, the exclusion zone 140 is defined by four distinct planar light beams 250A, 250B, 250C, and 250D, each extending parallel to a beam axis 121 from a respective one of line sources 260A, 260B, 260C, and 260D. The planar beams 250A, 250B, 250C, and 250D together define a rectangular cross-section parallelepiped exclusion zone 140 extending along a beam axis 121. The exclusion zone 140 is defined by a number of planar barriers, defined by the planar light beams 250A–250D. As in the exclusion zone 140 described in conjunction with FIG. 3A, each of the beams 250A, 250B, 250C, and 250D may for example be formed from a linear array of light sources (such as lasers or LEDs), or from a swept single light source.

In one exemplary embodiment of the invention, the exclusion zone 140 is not a static zone, but rather is a variable dimension zone. In other words, the exclusion zone is defined by boundaries that are movable, and the dimensions of the exclusion zone 140 can be modified in near real time. In this embodiment, one or more barriers defining an exclusion zone may be selectively disabled, e.g. in a planar dimension. For example, one or more planar barriers defining the exclusion zone 140 may be selectively disabled, thereby changing the dimensions of the exclusion zone 140.

Figure 4:
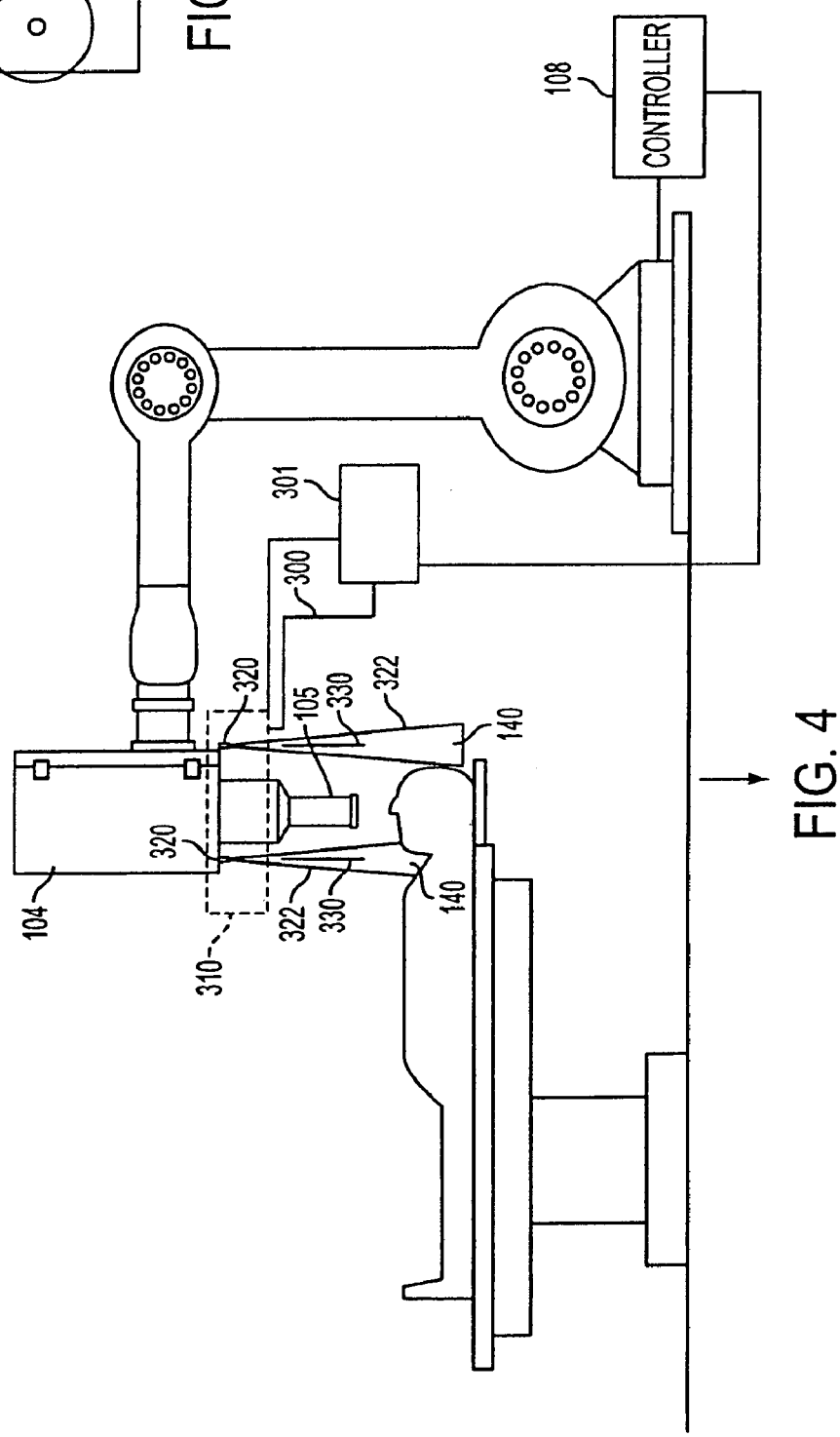
FIG. 4 illustrates a collision avoidance subsystem, constructed in accordance with another embodiment of the present invention, and including an array of acoustic transducers.

FIG. 4 illustrates a collision avoidance subsystem 300, constructed in accordance with another embodiment of the present invention, and including an array 310 of acoustic transducers 320. In the illustrated embodiment, the exclusion zone 140 is implemented via the array of acoustic transducers 320. The transducers 320 are capable of determining the distance to the nearest object, preferably at 6 to 80 inches therefrom. In one form, the transducers 320 ping to determined the distance to the nearest object. The acoustic transducers 320 may be ultrasonic transducers, by way of example.

In the illustrated embodiment, the array 310 of acoustic transducers 320 is fixedly coupled to the x-ray emission head of the linac 104. Each of the transducers 320 transmits a succession of acoustic pulses 322 along a transmission axis 330 extending from the linac 104. Each transducer detects acoustic energy back-scattered along the transmission axis 330 from any object disposed along the transmission axis. The subsystem 300 includes software for mutually aligning the beam axes (prior to operation of the subsystem 300)*t* whereby cross-sections of adjacent pairs of pulses 322 transverse to the transmission axis 330 are contiguous at a predetermined distance from the head 105 to minimize gaps in the covered area.

The collision avoidance subsystem 300 includes software 301 for determining, from the received back-scattered acoustic energy, the distance between the linac and the object. In response to the determined distance being at or less than a predetermined value, the software sends signals to the controller 108*t* instructing the controller to interrupt any further motion of the head 105 toward the exclusion zone 140.

Figure 5A:
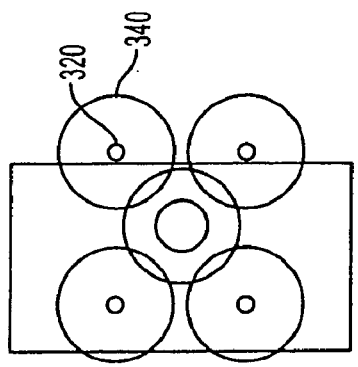
FIG. 5A illustrates an array of four ultrasonic transducers, arranged about an x-ray emission head in a rectangular pattern.

In an exemplary embodiment, an array of four ultrasonic transducers 320 are arranged about the base of the linac 104 in a rectangular pattern, as shown in FIG. 5A. In addition, the acoustic pulses 322 form a sense cone 340, as illustrated in FIGS. 5A and 58.

Figure 5B:
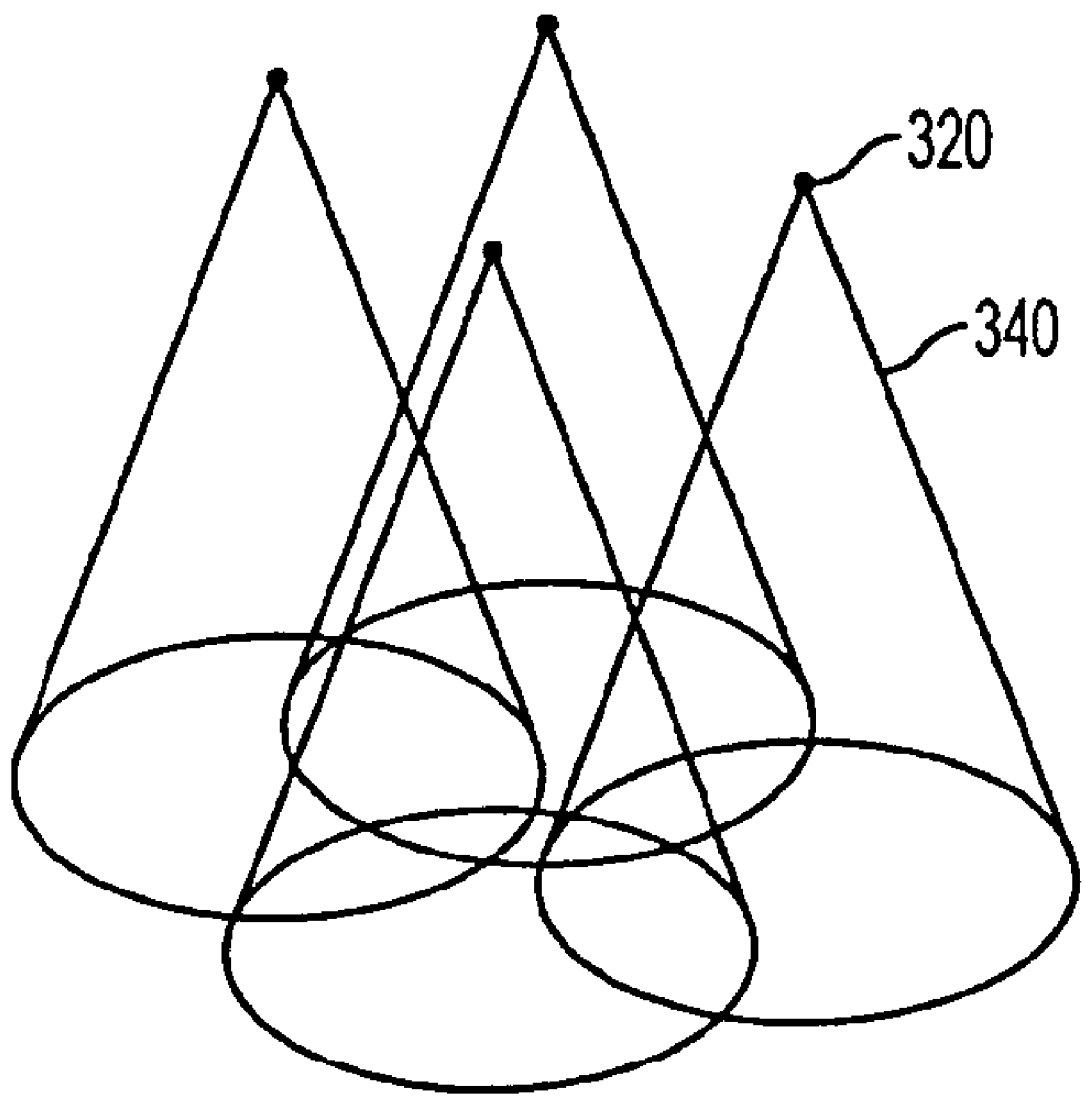
FIGS. 5B and 5C illustrate sense cones formed by the ultrasonic transducers shown in FIG. 5A.
Figure 5C:
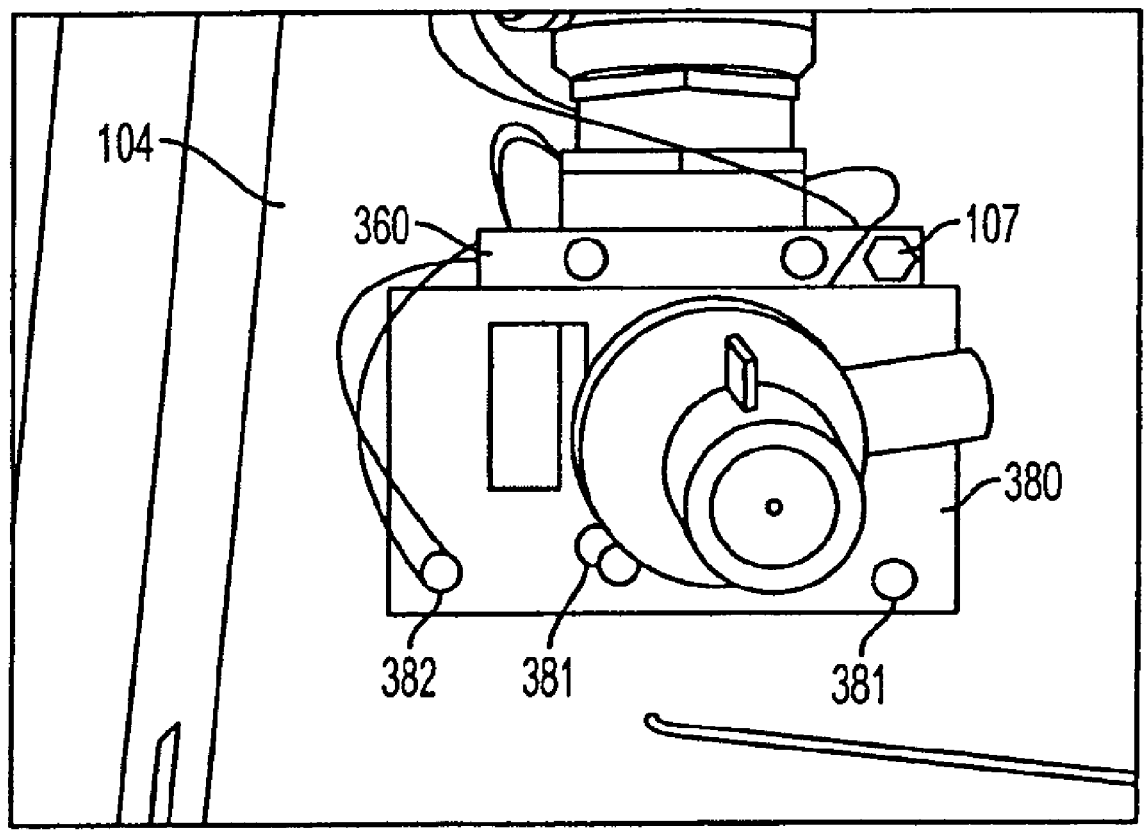

In the embodiment illustrated in FIG. 5C, the four ultrasonic sensors 320 are arranged around the housing of the collimator 107, so as to provide full coverage of the collimator at 24 inches. In particular, two of the sensors 320 are mounted on a base plate 360 of the linac 104, via existing holes 361 in the base plate 360. Two sensors are mounted on the cover 380 of the linac 104. The cover thus includes three holes that are cut therein, two holes 381 for the sensors and one hole 382 for wire exit.

Each ultrasonic sensor 320 determines the distance from the nearest object, when such distance ranges from 6 to 80 inches. Each sensor reports an analog voltage value corresponding to the sensed distance, ranging from 0 to 10 volts: 0 volts indicates 6 inches to the nearest object, whereas 10 volts indicates 80 inches to the nearest object. Each sensor pings at 150 KHz, with a response time of 25 milliseconds, and is able to discern objects at plus or minus 10 degrees from the perpendicular view angle. Before operation, the input of all four sensors 320 are synchronized, in order to prevent crosstalk between the sensors. The sensors 320 may be connected to the analog input on the robot 102. In one form, the sensors may be manually disabled by a switch.

Figure 6:
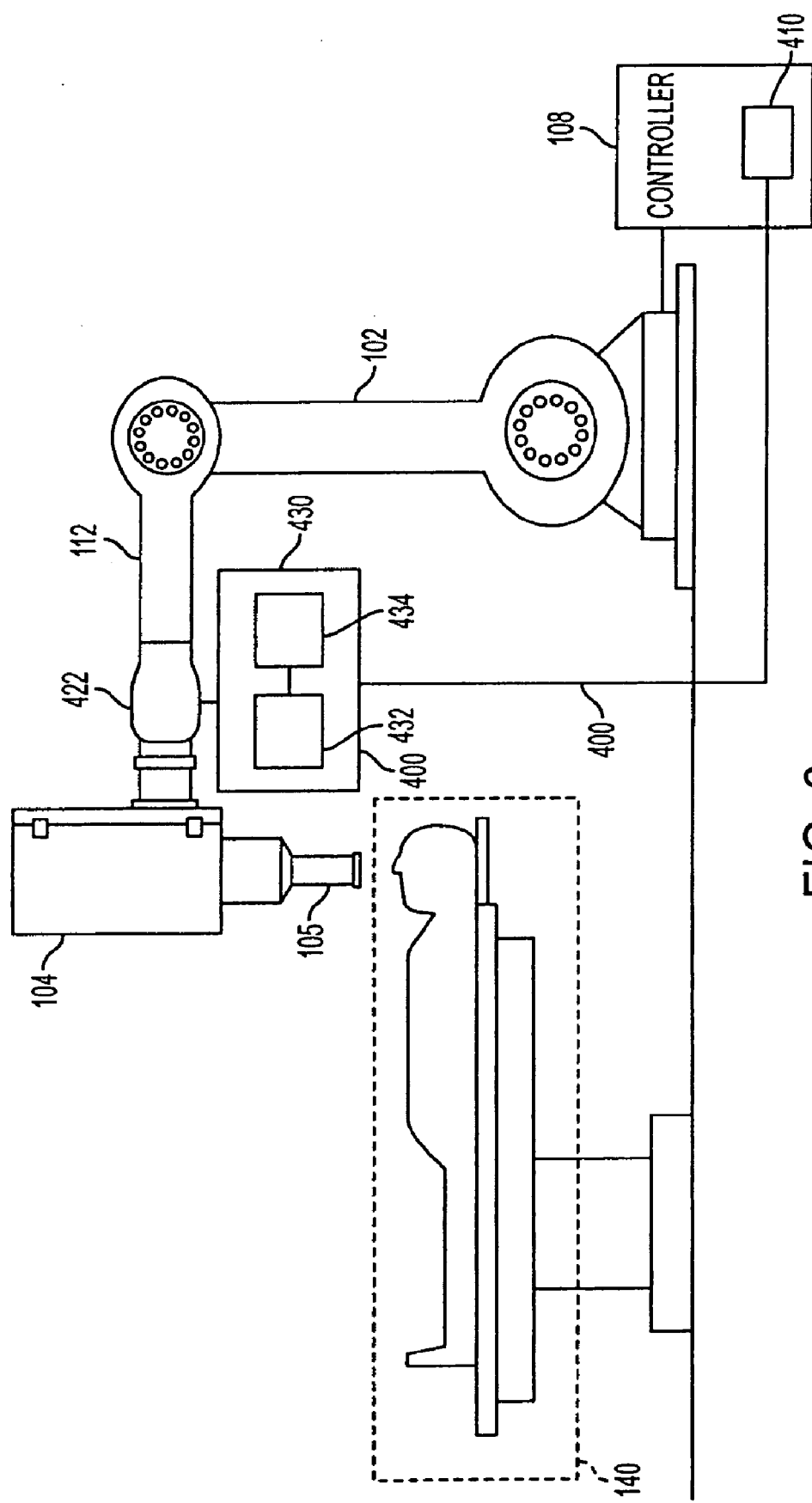
FIG. 6 illustrates a collision avoidance subsystem, constructed in accordance with another embodiment of the present invention, and including a tactile sensor.

FIG. 6 illustrates a collision avoidance subsystem 400, constructed in accordance with another embodiment of the present invention, and including a tactile sensor. In the embodiment illustrated in FIG. 6, the present invention implements the exclusion zone 140 with a sensor 430, which generates an indicative signal if and when it impacts with an object in the exclusion zone 140. In the illustrated embodiment, the sensor 430 is a tactile sensor, such as a pressure-sensitive pad; however, other types of sensors (including but not limited to infrared sensors and electrostatic capacitance sensors) may be used in other embodiments of the invention.

The tactile sensor 430 is disposed on a surface 422 of the articulated arm assembly 112 of the robot 102. The sensor 430 is operative to generate an alarm signal upon impact of sensor 430 with any object, during motion of the arm 112 and/or head 105. In a particular, in the illustrated embodiment the tactile sensor 430 includes a fluid-filled bladder 432, and a pressure transducer 434 coup]ed to the bladder 432 for generating the alarm signal, when fluid pressure in the bladder 432 exceeds a predetermined threshold. The controller 108 includes software, responsive to the alarm signal, for sending instructions to the robot to interrupt any further motion of the arm 112 and/or head 105.

The collision avoidance subsystems, described in the embodiments illustrated in FIGS. 4–6, may include software filters on the return signal, for minimizing false positive signals.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method, comprising:
   calculating a variable dimension exclusion zone of a radiosurgery system, the radiosurgery system comprising an x-ray source having an emission head and an arm assembly; and
   preventing at least one of the emission head or arm assembly from entering the variable dimension exclusion zone.

2. The method of claim 1, wherein calculating the variable dimension exclusion zone comprises defining one or more moveable boundaries as dimensions of the variable dimension exclusion zone.

3. The method of claim 2, further comprising changing the dimensions of the variable dimension exclusion zone.

4. The method of claim 3, wherein changing the dimensions of the variable dimension exclusion zone comprises selectively disabling one or more moveable boundaries of the variable dimension exclusion zone.

5. The method of claim 3, wherein the one or more moveable boundaries are planar barrier, and wherein changing the dimensions of the variable dimension exclusion zone comprises selectively disabling one or more planar barriers.

6. The method of claim 2, further comprising modifying the dimensions of the variable dimension exclusion zone during treatment.

7. The method of claim 6, wherein modifying the dimensions of the variable dimension exclusion zone comprises receiving feedback information from a patient positioning system.

8. The method of claim 6, wherein modifying the dimensions of the variable dimension exclusion zone comprises receiving feedback information from a controller of a radiosurgery system.

9. The method of claim 1, wherein preventing at least one of the emission head or arm assembly from entering the variable dimension exclusion zone comprises stopping any further motion of the at least one of emission head or arm assembly when the at least one of emission head or arm assembly reaches a boundary of the variable dimension exclusion zone.

10. The method of claim 1, wherein preventing the at least one of emission head or arm assembly from entering the variable dimension exclusion zone comprises:
    calculating an additional exclusion zone, wherein the additional exclusion zone is a first layer and the exclusion zone is a second layer, wherein the first layer is outside the second layer; and
    slowing down motion of the at least one of emission head or arm assembly upon reaching a boundary of the additional exclusion zone.

11. A method, comprising:
    establishing a exclusion zone of a radiosurgery system, the radiosurgery system comprising an x-ray source having an emission head;
    moving the emission head during treatment of a patient, wherein the exclusion zone travels with the emission head; and
    detecting a presence and location of an object in the traveling exclusion zone.

12. The method of claim 11, wherein the radiosurgery system comprises an arm assembly coupled to the x-ray source having the emission head, and wherein the exclusion zone travels with the arm assembly.

13. The method of claim 11, wherein the object comprises a part of the radiosurgery system.

14. The method of claim 11, wherein the object comprises a part of the patient.

15. The method of claim 11, wherein the object comprises a part of an equipment in a treatment room in which the radiosurgery system resides.

16. The method of claim 11, further comprising preventing the emission head from effecting a collision with the object in the traveling exclusion zone.

17. The method of claim 13, wherein preventing the emission head from effecting the collision comprises:
    detecting an intrusion of the object into the traveling exclusion zone; and
    preventing or slowing down further relative advance of the object in the traveling exclusion zone.

18. The method of claim 13, wherein preventing the emission head from effecting the collision comprises:
    detecting an intrusion of the object into the traveling exclusion zone; and
    preventing or slowing down further relative advance of the object in the traveling exclusion zone.

19. The method of claim 17, wherein detecting the intrusion of the object comprises using at least one of a laser rangefinder, one or more optical emitter-receiver pairs, an array of acoustic transducers, a capacitance sensor, or an infrared sensor to detect the intrusion of the object.

20. An apparatus, comprising:
    a radiosurgery system comprising an x-ray source having an emission head and an arm assembly; and
    a controller coupled to the radiosurgery system, the controller to calculate a variable dimension exclusion zone of a radiosurgery system, wherein the controller is configured to prevent at least one of the emission head or arm assembly from entering the variable dimension exclusion zone.

21. The apparatus of claim 20, wherein the controller is configured to define one or more moveable boundaries as dimensions of the variable dimension exclusion zone, and wherein the controller is configured to change the dimensions of the variable dimension exclusion zone.

22. The apparatus of claim 20, wherein the controller is configured to define one or more moveable boundaries as dimensions of the variable dimension exclusion zone, and wherein the controller is configured selectively disable one or more moveable boundaries of the variable dimension exclusion zone.

23. An apparatus, comprising:
    a radiosurgery system comprising an x-ray source having an emission head and an arm assembly; and
    means for calculating a variable dimension exclusion zone of a radiosurgery system.

24. The apparatus of claim 23, further comprising means for preventing at least one of the emission head or arm assembly from entering the variable dimension exclusion zone.

25. The apparatus of claim 23, further comprising means for changing the dimensions of the variable dimension exclusion zone.

26. An apparatus, comprising:
    means for establishing a exclusion zone of a radiosurgery system, the radiosurgery system comprising an x-ray source having an emission head;
    means for moving the emission head during treatment of a patient, wherein the exclusion zone travels with the emission head; and
    means for detecting a presence and location of an object in the traveling exclusion zone.

27. The apparatus of claim 26, further comprising means for preventing the emission head from effecting a collision with the object in the traveling exclusion zone.

28. The apparatus of claim 26, further comprising:
    means for detecting an intrusion of the object into the traveling exclusion zone; and
    means for preventing or slowing down further relative advance of the object in the traveling exclusion zone.

* * * * *

UNITED STATES PATENT AND TRADEMARK OFFICE
CERTIFICATE OF CORRECTION

| | | |
|---|---|---|
| PATENT NO. | : 7,103,144 B2 | Page 1 of 1 |
| APPLICATION NO. | : 11/338120 | |
| DATED | : September 5, 2006 | |
| INVENTOR(S) | : Wong et al. | |

It is certified that error appears in the above-identified patent and that said Letters Patent is hereby corrected as shown below:

On the Title page of the above-identified patent, after "(22) Filed: Jan. 23, 2006," please insert the following statements:

Related U.S. Application Data
--This application is a continuation of U.S. Application No. 10/814,451, filed March 31, 2004.--

Signed and Sealed this

Twenty-first Day of August, 2007

JON W. DUDAS
*Director of the United States Patent and Trademark Office*